(12) United States Patent
Palumbo

(10) Patent No.: US 9,713,928 B2
(45) Date of Patent: Jul. 25, 2017

(54) DECORATION LINE

(71) Applicant: PROJECTA ENGINEERING S.R.L., Fiorano Modenese (Modena) (IT)

(72) Inventor: Vincenzo Palumbo, Fiorano Modenese (IT)

(73) Assignee: PROJECTA ENGINEERING S.P.A., Fiorano Modenese (Modena) (IT)

( * ) Notice: Subject to any disclaimer, the term of this patent is extended or adjusted under 35 U.S.C. 154(b) by 0 days.

(21) Appl. No.: 15/028,613

(22) PCT Filed: May 30, 2014

(86) PCT No.: PCT/IB2014/061852
§ 371 (c)(1),
(2) Date: Apr. 11, 2016

(87) PCT Pub. No.: WO2015/052596
PCT Pub. Date: Apr. 16, 2015

(65) Prior Publication Data
US 2016/0297209 A1 Oct. 13, 2016

(30) Foreign Application Priority Data

Oct. 11, 2013 (IT) .............................. VR2013A0226

(51) Int. Cl.
*B41J 3/407* (2006.01)
*B41J 29/393* (2006.01)
(Continued)

(52) U.S. Cl.
CPC ........... *B41J 3/4073* (2013.01); *B28B 11/001* (2013.01); *B28B 11/044* (2013.01);
(Continued)

(58) Field of Classification Search
CPC ........ B41J 2/407; B41J 2/4073; B41J 2/2114; B41J 29/38; B41J 29/387; B41J 29/393; B41J 2029/3935
See application file for complete search history.

(56) References Cited

U.S. PATENT DOCUMENTS 2,277,005 A * 3/1942 Ruse ................. C03C 17/02
427/209
6,292,635 B1 * 9/2001 Tokairin ............. B41J 11/008
399/15

(Continued)

FOREIGN PATENT DOCUMENTS

CN 201819669 5/2011
IT RE20110012 8/2012
(Continued)

*Primary Examiner* — Geoffrey Mruk
*Assistant Examiner* — Scott A Richmond
(74) *Attorney, Agent, or Firm* — Tuntunjian & Bitetto, P.C.

(57) ABSTRACT

A line for decorating and controlling products, in particular ceramic tiles and the like, includes a conveyor of products to be decorated, at least one decorating device of the jet type actuated by piezoelectric-control nozzles adapted to apply at least one layer of enamel on the products passing on said conveyor; the line further includes at least one control and diagnostic module of the decorated products, provided with means for detecting decoration and/or structural defects of the products themselves.

17 Claims, 1 Drawing Sheet

(51) Int. Cl.
*B41J 11/00* (2006.01)
*B28B 11/00* (2006.01)
*B28B 11/04* (2006.01)
*B28B 17/00* (2006.01)
*G01N 21/25* (2006.01)
*G01N 21/89* (2006.01)
*G01N 21/892* (2006.01)
*G01J 3/50* (2006.01)
*G01B 11/06* (2006.01)
*G01N 21/3563* (2014.01)
*G01N 21/31* (2006.01)
*G01N 21/88* (2006.01)
*B05B 12/08* (2006.01)

(52) U.S. Cl.
CPC .......... *B28B 17/0072* (2013.01); *B41J 3/407* (2013.01); *B41J 11/0095* (2013.01); *G01J 3/501* (2013.01); *G01N 21/25* (2013.01); *G01N 21/251* (2013.01); *G01N 21/88* (2013.01); *G01N 21/8901* (2013.01); *G01N 21/892* (2013.01); *B05B 12/084* (2013.01); *G01B 11/0616* (2013.01); *G01N 21/3563* (2013.01); *G01N 2021/3155* (2013.01); *G01N 2021/8845* (2013.01)

(56) References Cited

U.S. PATENT DOCUMENTS

| | | | |
|---|---|---|---|
| 6,419,342 B1* | 7/2002 | Bronswijk | B41J 2/2135 347/19 |
| 2002/0135692 A1* | 9/2002 | Fujinawa | G02B 7/36 348/335 |
| 2006/0066653 A1* | 3/2006 | Konno | B41J 2/2114 347/14 |
| 2008/0239284 A1 | 10/2008 | Vahey et al. | |
| 2009/0029296 A1* | 1/2009 | Suzuki | B41J 2/465 430/322 |
| 2009/0213157 A1* | 8/2009 | Obertegger | B41J 2/16588 347/14 |
| 2012/0314222 A1 | 12/2012 | Stone et al. | |
| 2013/0335753 A1* | 12/2013 | Okamoto | G06F 3/1211 358/1.2 |

FOREIGN PATENT DOCUMENTS

| | | |
|---|---|---|
| JP | 2002160432 | 6/2002 |
| WO | 2012164758 | 12/2012 |

\* cited by examiner

DECORATION LINE

TECHNICAL FIELD OF THE INVENTION

The present invention relates to a decoration line.

More particularly, the present invention relates to a decoration line which is fully digitally managed and controlled for products such as ceramic tiles and the like.

BACKGROUND OF THE INVENTION

In the field of production of ceramic tiles and the like decoration lines are normally used which apply enamels to the surface of the ceramic substrate, adapted to create both a certain aesthetic and decorative effect and a functional result of protection and coverage of the substrate itself.

The enamels can be applied on the ceramic substrate with different technologies, e.g. using digital or analog devices. Analog devices are those of the traditional type which employ devices whose application functionality and the respective adjustment, for the purposes of the enameling process, is essentially mechanical: for example, bells or spray guns for full coating or screen printing or flexo roll decorating devices. Digital devices are those that apply enamel on the ceramic substrate by means of heads delivering a jet actuated by piezoelectrically-controlled nozzles or other type of nozzles, which actuation and adjustment are digitally driven for the purposes of the decoration process.

With particular but not exclusive reference to digital decorating devices, it is noted that nowadays the graphics resolution obtainable in the product application can also be very high: in fact, the current technologies allow simulating, with truly amazing results, natural materials such as wood, marble, granite or the like.

Therefore, the issue of the control and verification of the result obtained by the decorating devices, both in terms of quality of the product surface appearance and in terms of physical and mechanical characteristics of the layer or layers of enamel applied, is of primary importance.

SUMMARY OF INVENTION

The technical task of the present invention therefore is to improve the prior art.

Within this technical task, an object of the present invention is to develop a decoration line that allows controlling, in real time, the quality of the result obtained on each of the decorated products.

Yet another object of the present invention is to provide a decoration line which allows to automatically discard decorated products that have defects of various kinds.

This task and these objects are achieved by the decoration line according to the present principles.

The present application refers to preferred and advantageous embodiments of the invention.

BRIEF DESCRIPTION OF THE DRAWINGS

The features of the invention will be better understood by any skilled person from the following description and from the appended drawings, given by way of a non-limiting example, in which.

DETAILED DESCRIPTION OF EMBODIMENTS OF THE INVENTION

Figure 1:
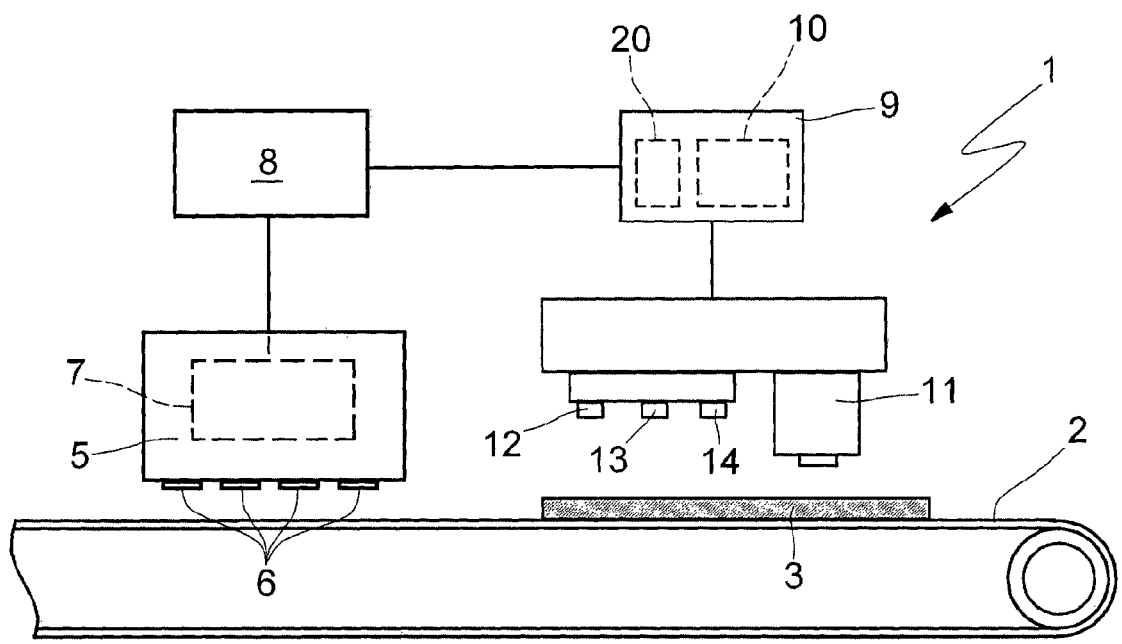
FIG. 1 is a lateral detailed view of a decoration line according to the invention.

With reference to the accompanying FIG. 1, a decoration line according to the present invention is globally indicated with reference numeral 1.

The decoration line is particularly but not exclusively intended for the application of enamel on products such as ceramic tiles and the like; however, the decoration line has an absolutely general use and could also be used for other types of ceramic products without any limitation.

More in detail, the decoration line according to the present invention is preferably intended for the application of enamel on so-called raw ceramic tiles, that is, not yet subjected to a baking process in the kiln. However, the line may also be used to apply enamel on tiles already baked in the kiln.

The decoration line 1 according to the invention comprises a conveyor 2 of products 3 on which one or more layers of enamel 4 are to be applied. As said, products 3 preferably consist of ceramic tiles but can also be products of another type. Conveyor 2 is, for example, of the belt type but could also be another type known in the field without limitation to the objects of the present invention.

Products 3 traveling on conveyor 2 come, for example, from a drying station of the production line and once decorated are then intended to be subsequently introduced into a baking kiln.

According to an aspect of the present invention, the decoration line comprises at least one decorating device 5.

The above mentioned decorating device 5 is of the jet type actuated by piezoelectric-control nozzles.

The above decorating device 5 is, in more detail, adapted to apply on the products 3 moving on conveyor 2, at least one layer of vitreous enamel 4 in suspension in a liquid suspending agent adapted to be processed in a digital decorating system of the substantially continuous field type, for the creation of a basecoat or topcoat on products 3.

For a better understanding of the invention, it is noted that the decorating device 5 is, for example, of the type described in Italian patent application n. RE2011A000012 by the same Applicant. However, the decorating device 5 could also be of another type.

For example, in other embodiments of the invention, the decorating device 5 could be of the analog type or of yet another type without limitation to the objects of the present invention.

The piezoelectrically-controlled nozzles which apply the layer of enamel 4 are provided—in a per se known manner—on heads 6 which directly face the upper surface of conveyor 2 and which, in use, are located at a predetermined distance—for example few millimeters—from the upper surface of products 3.

Typically, each of the heads 6 installed on the decorating device 5 corresponds to a single type of enamel applicable on the surface of products 3, or to a single color of enamel, et cetera.

The enamel dispensing system, through heads 6 of the decorating device 5, is, in any case, suitable for applying flows of enameling carrier having high capacity and low resolution, that is, suitable for creating basecoats or topcoats even with relatively large amounts of material.

This is substantially obtained by multiplying the number of heads 6 until the desired amount of enameling carrier is obtained.

In FIG. 1, the decorating device 5 comprises four heads 6, this number is to be considered by way of a non-limiting example.

In fact, a decorating device 5 with a single head 6 could, however, be used in relation to specific application and/or economic requirements.

In the case of a single head 6, the required amount of enameling carrier will be dispensed in a substantially longer time.

As said, the enameling carrier is of the vitreous enamel type in suspension in a suspending agent adapted to be processed in a digital decorating system.

In some embodiments of the invention, the decoration line 1 can comprise multiple decorating devices 5, also of different type, arranged in series or in parallel, without any limitation.

Of course, the choice of the type of decorating devices 5, which make up the line depends on various factors such as the type of product 3 to be decorated, the type of decoration to be made on product 3, the sequence of application of the various enamels, and others.

Obviously, these factors also affect the sequence according to which the various devices are arranged in the decoration line.

The decorating device 5 is provided with a respective local control unit 7, which manages basic operating parameters of device 5 itself.

The decoration line 1 according to the invention comprises a supervision unit 8 of the line operation.

The local control unit 7 of the decorating device 5 is operatively interlocked to said supervision unit 8.

According to an aspect of the present invention, the decorating line 1 comprises at least one control and diagnostic module 9 of the decorated products 3.

The control and diagnostic module 9 is operatively connected to the supervision unit 8.

According to another aspect of the present invention, the control and diagnostic module 9 comprises means 10 for detecting decoration and/or structural defects of products 3.

As will be explained below, the methods of detection of defects of products 3 detect problems related to the quality of the decoration or structural problems, through an intelligent diagnostics that identifies and limits the single defect without having to check the entire surface of product 3, as instead occurs in the application of other diagnostic techniques.

More in detail, the means 10 for detecting defects comprise at least one viewing device 11.

The viewing device 11 comprises, in a preferred embodiment of the invention, at least one camera of the linear type, for example comprising a CCD (charge-coupled device) linear image sensor.

This type of camera has, among others, compared to other types of devices, the advantage of being able to carry out the control of product 3 in a very short time, a feature that is crucial in this type of application.

Moreover, linear cameras can provide a high spatial resolution not obtainable with matrix cameras. According to another aspect of the invention, the control and diagnostic module 9 comprises lighting means 12, 13, 14 of the decorated products 3.

In particular, the lighting means 12-14 are suitable for emitting at various frequencies, for the purposes which will be better explained later.

The lighting means 12-14 comprise, in more detail, one or more first lighting means 12 which are designed to emit white light.

These first lighting means 12 allow capturing the image of the decorated product 3 with sufficient accuracy by the viewing device 11.

In particular, the first white light lighting means 12 can be used to light products decorated with not too clear shades.

The lighting means 12-14 also comprise, according to another aspect of the present invention, one or more second lighting means 13 that emit blue light.

The second lighting means 13, emitting blue light, are instead used for illuminating products 3 decorated with light or mainly bright shades, because they allow to better highlight color differences existing on the product 3 surface.

According to yet another aspect of the present invention, the lighting means 12-14 comprise third lighting means 14 which emit infrared radiation.

In particular, the third infrared radiation lighting means 14 can allow detecting, with good accuracy, the thickness of the enamel layer 4 applied on products 3.

In fact, the employed viewing device 11—linear camera, which, as said above, is for example of the CCD type—is sensitive to infrared radiation.

The means 10 for detecting defects include, more particularly, means for detecting at least one chromatic peak in the image of a decorated product 3 detected by the viewing device 11.

Figure 2:
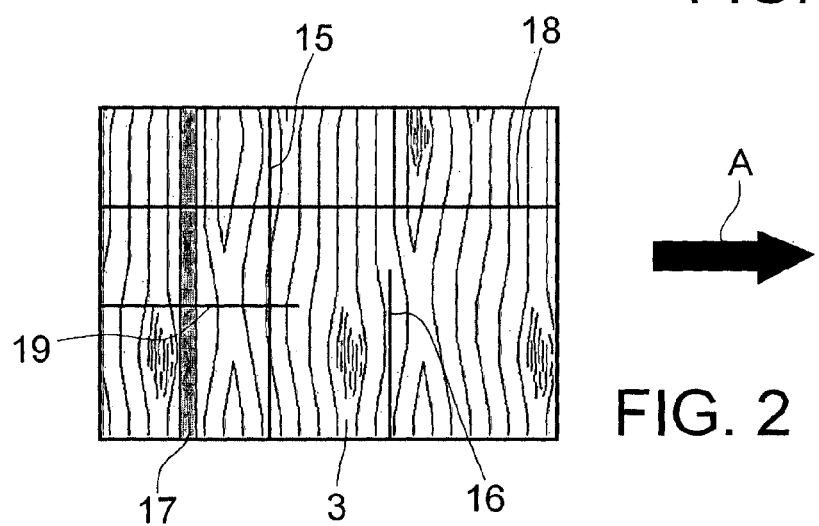
FIG. 2 is a top view of a decorated product having decoration defects.
Figure 3:
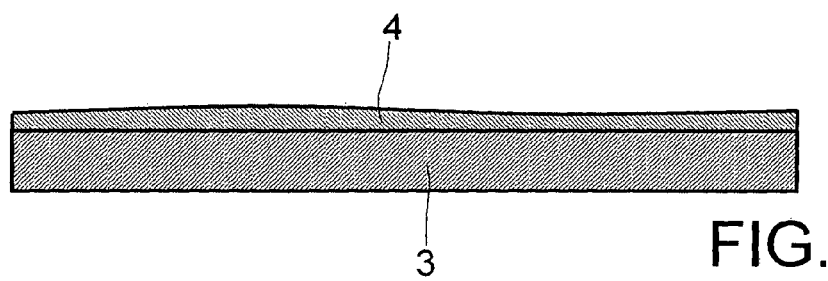
FIG. 3 is a lateral view of a decorated product.

For a better understanding, reference is made to FIG. 2, where a decorated product 3 is schematically represented showing chromatic defects 15, 16, 17, 18, 19 are present.

For example, a first type of chromatic defect 15 of product 3 can be a thin strip transverse to the advancement direction A of product 3 on conveyor 2, and having a length substantially equal to the width of product 3 itself.

A second type of chromatic defect 16 can be a thin strip transverse to the advancement direction A of product 3 on conveyor 2, and having a length shorter than the width of product 3 itself.

A third type of chromatic defect 17 can be a band transverse to the advancement direction A of product 3 on conveyor 2, having a certain width and a length equal to the width of product 3 itself or even smaller.

A fourth type of chromatic defect 18 of product 3 can be a thin strip parallel to the advancement direction A of product 3 on conveyor 2, and having a length substantially equal to the length of product 3 itself.

A fifth type of chromatic defect 19 of product 3 can be a thin strip parallel to the advancement direction A of product 3 on conveyor 2, and having a length shorter than the length of product 3 itself. Of course, the above types of defects 15-19 are given only by way of example.

Other defects can consist of spots, dots or by combinations of all the above types.

In the practice, a chromatic defect is understood to be a more or less extensive area of the surface of the decorated product 3, wherein the coloring is not as desired.

Each of the above types of defects 15-19 generates, in the image of product 3 detected by the viewing device 11, a chromatic peak.

The viewing device 11, which as said consists of a linear camera, then acquires a line of pixels corresponding to a line of the product surface, each of which characterized by its own color.

Following the passage of product 3 under the linear camera, an overall image of the product is thus formed and a respective pattern of the spectrum of the product image is obtained.

Each defect 15-19 that can be present in product 3 therefore originates one or more pixels—obviously in relation to the defect extension—marked by a coloring that is clearly different from that of the remaining area of product 3 itself. This causes a change in the pattern of the spectrum of the product image compared to that of normal conditions.

This change in the spectrum pattern generates an alarm signal, which is managed by the control and diagnostic module 9 in the way explained hereafter.

It is noted that with this technique it is also possible to detect any structural defects such as for example lumps, chippings, scratchings, cracks and breakings in product 3.

It is also possible to detect areas where the enamel layer 4 is not properly applied.

In fact, such defects can be detected, by the viewing device 11, as areas of different color than the rest of the surface of product 3. The control and diagnostic module 9 comprises means 20 for interrupting the operation of the decoration line 1 following the identification of one or more products characterized by chromatic peaks indicating a chromatic defect, according to the methods described above.

Such operation interruption means 20 can be actuated, for example, following a precise instruction of the user who manages the operation of line 1.

For example, the user can set the control and diagnostic module 9 in such a way that the interruption means 20 are actuated only when defects 15-19 detected on a product 3 by the detection means 10 have an extent exceeding a certain minimum value predetermined by the user himself.

Or, the user can decide to set the control and diagnostic module 9 so that the interruption means 20 intervene whenever the detection means 10 detect a defect 15-19 of any extent in product 3.

In another alternative, the user can decide to set the control and diagnostic module 9 so that the interruption means do not intervene even if the detection means 10 detect the presence of defects 15-19 on product 3.

Obviously, the user will choose between all these alternatives according to the quality level to be obtained on products 3, or in relation to whether he wants to accept or not products with defects 15-19, even of a very small extent.

Furthermore, the user can decide to set the control and diagnostic module 9 in such a way that the interruption means 10 intervene only after that a same defect 15-19, or more defects 15-19 have been identified in a sequence consisting of a certain number of products 3.

In other words, the user can decide to accept a defect 15-19 that occurs sporadically or on a limited number of products 3, while he could instead decide to interrupt the operation of the decoration line 1 only in the case where defect 15-19 is systematically present in a certain sequence of products 3.

The user can conveniently combine this intervention mode with that relating to the evaluation of the extent of defects 15-19, that is, for example, interrupt the operation only after a certain sequence of products 3 has at least one defect 15-19 larger than a certain extent.

According to another aspect of the present invention, the control and diagnostic module 9 comprises means for executing a test printout.

In particular, such means execute a test printout of the decoration—i.e. the layer of enamel 4—to apply on products 3.

The means of executing a test printout can be controlled to operate following an instruction of an interruption of the decoration line 1, in the manner described above.

The execution of the test printout is intended to allow the control and diagnostic module 9 to detect the presence of problems in the operation of the decorating device 5, and in particular in the printing heads 8.

In fact, often, from the simple observation of the decorated product 3 it is not possible to understand the exact extent of defect 15-19 and especially what trouble or inconvenience may have caused it.

The test printout is compared graphically by the control and diagnostic module 9 with a reference image without defects of the same test printout.

In this case, the comparison is made in detail on the entire area concerned, for example, pixel by pixel.

According to a simplified version of the present invention, the comparison could also be made manually by a person responsible for such a check.

This comparison therefore allows to very precisely identify the single nozzles of heads 6 which have operating problems, and acting accordingly.

For example, a cleaning cycle of the nozzles of heads 6 may be started if the problem is due to a blockage of one or more nozzles.

According to yet another aspect of the present invention, the control and diagnostic module 9 of the decoration line 1 includes means for measuring the thickness of the enamel layer 4 applied on products 3.

Such measuring means check that the layer 4 deposited has the desired thickness in all areas of the surface of product 3.

More specifically, the means for measuring the thickness of enamel 4 include the viewing device 11 and said one or more third lighting means 14 that emit infrared radiation.

In other embodiments of the invention, the means for measuring the thickness of enamel 4 can consist of an independent module.

In the practice, the viewing device 11 acquires the image reflected by product 3 hit by the infrared radiation and is therefore able—obviously through appropriate programs provided in the supervision unit 8 of the decoration line 1—to determine with sufficient accuracy the thickness of layer 4 in all areas of the surface of product 3.

The decoration process implemented by the line according to the invention is therefore as follows. Products 3 coming from a drying station advance on conveyor 2. The decorating device 5 then applies on each of the respective products 3 at least one layer of enamel 4.

The enamel layer 4 is, as mentioned, for example of the vitreous type in suspension in a liquid suspending agent adapted to be processed in a digital decoration system substantially of the continuous field type, for the creation of a basecoat or topcoat on the products.

Products 3 can then advance towards one or more other decorating devices 5 provided in line 1.

The operation of the decorating device 5 or of the various decorating devices is managed by the respective local control station 7.

At the end of decoration step, products 3 are then analyzed by the control and diagnostic unit 9 which, as told, is intended to locate any defects 15-19, both of decoration and structural type, in products 3.

The check takes place by actuating the viewing device 11 and one or more of lighting means 12-14, in relation to the features of product 3 and to the type of checks to be carried out.

The viewing device 11 then captures an image of the decorated product 3 suitably lighted by one or more lighting means 12-14.

For example, the first lighting means 12 can be actuated which emit white light for a surface check of a product 3 decorated with shades that are not too light.

The second lighting means 13 can be actuated instead, which emit blue light, for a surface check of a product 3 decorated with clear shades.

The third lighting means 14, which emit infrared radiation, can also be activated to check the thickness of the enamel layer 4.

The detecting means 10 detect, as described above, any defects 15-19 on the surface of products 3.

Upon detecting one or more defects 15-19 on product 3, the control and diagnostic module 9 works according to the instructions given by the user.

Based on the extent of the defect or defects 15-19 detected, and the frequency with which this occurs in a certain sequence of products 3, the control and diagnostic module 9 can stop the operation of the decoration line 1 and possibly launch a test printout to determine the problem that caused defect 15-19.

Optionally, the control and diagnostic module 9 can initiate a cleaning cycle of the print heads 6 of the decorating device 5.

It is also noted that the control and diagnostic module 9, for proper identification and definition of defects 15-19, is able to check the surface of product 3 having a certain color shade.

For example, if a defect is detected which consists of a strip or transversal band of a different color, such as a defect identified with numerals 15, 17 in FIG. 2, the control and diagnostic module 9 could interpret the chromatic peak associated with such a defect 15, 17 as a space between two successive products 3 that advance on conveyor 2.

To prevent this error, the control and diagnostic module 9 verifies the colored surfaces of product 3 to compare them with the theoretical surface of product 3 itself.

If the colored surfaces detected are less extensive than the theoretical surface of product 3, this means that there is a defect 15, 17 on the product itself.

The management of defective products 3 can provide for their automatic reject or forwarding, downstream of the decoration line, of products 3 themselves in different groups corresponding to different quality levels of finish.

It has thus been seen that the invention achieves the intended objects.

The decoration line 1 according to the present invention allows detecting chromatic or structural defects on decorated products 3 accurately and in real time during the operation of the line, in times well below those of other diagnostic systems.

In fact, the defects are detected through a quick and accurate chromatic analysis, which recognizes and circumscribes the defects and prevents having to check the entire surface of the products.

The line is also extremely versatile in terms of functionality and management capabilities of the defective products 3.

The above results are obtained with a constructive solution which is extremely simple, cost-effective and easy to control and manage.

The present invention has been described according to preferred embodiments but equivalent versions may be conceived without departing from the scope of protection offered by the following claims.

The invention claimed is:

1. A decoration and control line for products, comprising:
a conveyor of the products to be decorated;
at least one decorating machine of the jet type actuated by piezoelectrically controlled nozzles, suitable for applying at least one layer of enamel onto the products passing on said conveyor;
further comprising at least one control and diagnostics module of the decorated products, equipped with means for identifying decorative and/or structural defects of the products themselves, wherein said at least one control and diagnostics module further comprises a means for measuring a thickness of the at least one layer of enamel applied onto the products.

2. The decoration line according to claim 1, wherein said means for identifying defects comprise at least one viewing device.

3. The decoration line according to claim 2, wherein said means for identifying defects comprise means for detecting at least one chromatic peak in the image of a product detected by said viewing device.

4. The decoration line according to claim 2, wherein said viewing device comprises at least one linear video camera.

5. The decoration line according to claim 1, wherein said means for measuring the thickness of said enamel layer comprise a viewing device and one or more lighting means.

6. The decoration line according to claim 1, wherein said control and diagnostics module comprises lighting means for illuminating the products, said means being suitable for emitting according to various frequencies.

7. The decoration line according claim 6, wherein said lighting means comprise one or more first lighting means which emit white light.

8. The decoration line according to claim 6, wherein said lighting means comprise one or more second lighting means which emit blue light.

9. The decoration line according to claim 1, wherein said means for measuring a thickness comprise one or more third lighting means, which emit infrared radiation.

10. The decoration line according to claim 1, wherein said control and diagnostics module comprises interruption means for interrupting the operation of the line following identification of one or more products having defects formed by chromatic peaks.

11. The decoration line according to claim 10, wherein said control and diagnostics module comprises means for carrying out a test print after the interruption of the decoration line, due to the detection of a sequence of products having at least one defect.

12. The decoration line according to claim 1, wherein said machine is of the jet type actuated by piezoelectrically controlled nozzles, said line being suitable for applying onto the products moving on said conveyor at least one layer of enamel of the vitreous type in suspension in liquid suspension agent and suitable for being processed in a digital decorative system, said enamel layer being of the substantially continuous field type for the creation of a basecoat or a topcoat on the products, or being of the substantially discontinuous field type, for the creation of decorative or finishing effects on products.

13. A decoration and control process for products, comprising the steps of:
applying at least one enamel layer onto each product;
acquiring an image of the decorated product;
detecting the presence of possible defects consisting of chromatic peaks on the surface of the product; and measuring a thickness of said enamel layer applied onto each product.

14. The process according to claim 13, comprising a step of interrupting the operation of the line following the detection of at least one defect on at least one product.

15. The process according to claim 14, comprising a step of carrying out a test print of the decoration of the product after the interruption of the decoration line.

16. The process according to claim 15, comprising a step of comparing the test print of the decoration of the product with a defect-free reference image of the same test print.

17. A decoration and control line for products comprising:
a conveyor of the products to be decorated;
at least one decorating machine of the jet type actuated by piezoelectrically controlled nozzles, suitable for applying at least one layer of enamel onto the products passing on said conveyor;
further comprising at least one control and diagnostics module of the decorated products, equipped with means for identifying decorative and/or structural defects of the products themselves,
wherein said control and diagnostics module comprises lighting means for illuminating the products, said means being suitable for emitting according to various frequencies, and wherein said lighting means comprise one or more third lighting means, which emit infrared radiation, and further comprising means for measuring the thickness of said enamel layer.

* * * * *